(12) United States Patent
Kalvins et al.

(10) Patent No.: US 7,078,418 B1
(45) Date of Patent: Jul. 18, 2006

(54) 1-AZIRIDINO-1-HYDROXYIMINOMETHYL-DERIVATES, METHOD FOR THE PRODUCTION THEREOF AND MEDICAMENTS CONTAINING SAID COMPOUNDS

(75) Inventors: Ivars Kalvins, Miera Strasse 4-11, Lv-1063, Riga (LV); Viktor Adrianov, Riga (LV); Irina Shestakova, Riga (LV); Iveta Kanepe, Riga (LV); Ilona Domracheva, Riga (LV)

(73) Assignee: Ivars Kalvins, Ikskile (LV)

( * ) Notice: Subject to any disclaimer, the term of this patent is extended or adjusted under 35 U.S.C. 154(b) by 0 days.

(21) Appl. No.: 10/089,039

(22) PCT Filed: Sep. 22, 2000

(86) PCT No.: PCT/DE00/03441

§ 371 (c)(1),
(2), (4) Date: Sep. 23, 2002

(87) PCT Pub. No.: WO01/21585

PCT Pub. Date: Mar. 29, 2001

(30) Foreign Application Priority Data

Sep. 24, 1999 (DE) ................................ 199 47 440

(51) Int. Cl.
*A61K 31/44* (2006.01)
*A61K 31/33* (2006.01)
*C07D 401/06* (2006.01)
*C07D 285/10* (2006.01)
*C07D 405/06* (2006.01)

(52) U.S. Cl. ..................... 514/336; 514/183; 514/340; 514/362; 546/268.1; 548/134; 548/962; 548/963

(58) Field of Classification Search ................ 514/183, 514/340, 362, 471; 546/268.1; 548/134, 548/962, 963
See application file for complete search history.

(56) References Cited

OTHER PUBLICATIONS

Eremeev, et al, 1982, Synthesis and Investingation of Aziridino Dioximes, 6, 369-374.*
Tsou et al., Synthesis of Possible Cancer Chemotherapeutic Compounds Based on Enzyme Approach. IV. Aziridine Derivatives, Jul., 1963, pp. 435-439.*
Musluoğlu et al. 'Synthesis and Characterization of 1,2-Bis(aziridin-N-yl)glyoxime and its Nickel (II), Palladium (II) and Cobalt (II) Complexes,' J. Chem. Research (S), p. 142-3 (1999) Chem. Abs.:115:48589u (1991).

* cited by examiner

*Primary Examiner*—Johann Richter
*Assistant Examiner*—Ebenezer Sackey
(74) *Attorney, Agent, or Firm*—Kriegsman & Kriegsman

(57) ABSTRACT

Described are new 1-aziridino-1-hydroxyiminomethyl derivatives with the general formula (I), wherein R is able to is a single bond or a linker moiety capable of covalently bonding two aziridine oxime groups, $R_1$ and $R_2$ independently of one another are selected from the group consisting of —H, —$CH_3$, —$C_2H_5$, —CN, —COOH, —$COOCH_3$, —$COOC_2H_5$, —$CONH_2$, or —$C_6H_5$ group, and n is the whole number 2, provided that $R_1$ and $R_2$ are not both —H and provided that $R_1$ is not —H if $R_2$ is —$CH_3$ and $R_1$ is not —$CH_3$ if $R_2$ is —H The compounds of general formula (I) show antitumor activity.

6 Claims, No Drawings

1-AZIRIDINO-1-HYDROXYIMINOMETHYL-DERIVATES, METHOD FOR THE PRODUCTION THEREOF AND MEDICAMENTS CONTAINING SAID COMPOUNDS

This application is a 371 of PCT/DE00/03441 Sep. 22, 2000.

This invention relates to 1-aziridino-1-hydroxyiminomethyl derivatives, methods for preparing them, and drugs containing these compounds.

Only bis(aziridine oxime) of Formula 1 is and its dimethyl homologue are known so far in the state of the art (Andrianov, V. G., Eremeev, A. V., Zh. Org. Khim (1991), 27, 11216; Eremeev, A. V., Piskunova, I. P., Andrianov, V. G., Liepins, E., Khim. Geterotsikl. Soedin (1982), (4) 48894; Musluoglu, E., Ahsen, V., J. Chem. Research (S) (1999), 142–143).

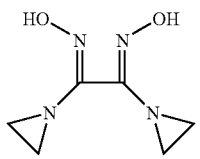

Nothing has yet been reported about the biological properties of this compound 1,1'-[1,2-bis(hydroxyimino)-1,2-ethanediyl]bisaziridine (1) or of its use as a drug.

Monoaziridine oximes that are used as herbicides, among others, are also known from DE-OS [Unexamined] 2,132,598. In the same way, aziridine oximes that are used to treat illnesses associated with the function of the chaperone system are described in WO 97/16439. However, nowhere have bis-, tris-, or even tetraaziridine oximes been described.

The object of this invention is to make available new 1-aziridino-1-hydroxyiminomethyl derivatives with the general formula I

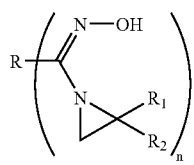

and a method for preparing them. Another object is to make available drugs that contain a compound with the general formula I.

In the general formula I, R stands for any organic residue that is able to bond covalently two aziridine oxime groups, $R_1$ and $R_2$ independently of one another stand for a hydrogen atom or a —$CH_3$, —$C_2H_5$, —CN, —COOH, —$COOCH_3$, —$COOC_2H_5$, —$CONH_2$, or —$C_6H_5$ group, and n is the whole number 2.

It is preferred for R to be selected from a single bond, linear or branched, saturated or unsaturated alkanes or heteroalkanes with up to 6 carbon atoms and with up to four hetero atoms, $C_3$–$C_8$ cycloalkanes that are optionally substituted with short-chain $C_1$–$C_6$ alkyl, $C_1$–$C_6$ alkoxy, nitro, amino, monosubstituted amino, and/or halogen groups, heterocyclic compounds with 3 to 6 ring atoms and up to four hetero atoms, aromatic compounds with up to 8 ring atoms that are optionally substituted with cyano, hydroxy, short-chain $C_1$–$C_6$ alkyl, $C_1$–$C_6$ alkoxy, nitro, amino, monosubstituted amino, trihaloalkyl, and/or halogen groups, and heteroaryls with 3 to 7 ring atoms and up to four hetero atoms.

It is particularly preferred for the parent substance R to be selected from a single bond, methyl, ethane, ethene, ethyne, propane, isopropane, butane, isobutane, sec-butane, pentane, isopentane, neopentane, hexane, azine, cyclopropane, cyclobutane, cyclopentane, cyclohexane, cycloheptane, cyclooctane, pyrrole, pyrroline, pyrrolidine, imidazole, imidazoline, pyrazolidine, thiazole, thiazoline, thiazolidine, isothiazole, isothiazoline, isothiazolidine, benzothiazole, furan, dihydrofuran, tetrahydrofuran, benzofuran, thiophene, benzothiophene, oxazole, oxazoline, oxazolidine, benzoxazole, isoxazole, isoxazoline, isoxazolidine, piperidine, piperazine, pyrimidine, morpholine, dihydropyran, tetrahydropyran, pyridazine, benzene, furoxane, imidazole, imidazoline, imidazolidine, pyrazole, pyrazoline, pyrazolidine, pyridine and its N-oxide, dihydropyridine, pyrimidine, or pyrazine. It is clear that the hetero atoms are positioned at any points in the ring. It is also preferred for $R_1$ and $R_2$ independently of one another to be hydrogen atoms or a —$CONH_2$ residue.

Very particularly preferred are
2,6-bis(1-aziridino-1-hydroxyiminomethyl)pyridine (6),
1,4-bis(1-aziridino-1-hydroxyiminomethyl)benzene (7),
1,4-di(α-2-carbamoylaziridino-α-hydroxyiminomethyl) benzene (8),
1,3-bis(1-aziridino-1-hydroxyiminomethyl)benzene (9),
1,3,5-tris(1-aziridino-1-hydroxyiminomethyl)benzene (10),
1,3-di(α-2-carbamoylaziridino-α-hydroxyiminomethyl) benzene (11),
2,6-di(α-2-carbamoylaziridino-α-hydroxyiminomethyl)pyridine (12),
3,5-bis(1-aziridino-1-hydroxyiminomethyl)pyridine (13),
2,5-bis(1-aziridino-1-hydroxyiminomethyl)pyridine ((14),
2,4-bis(1-aziridino-1-hydroxyiminomethyl)pyridine (15),
2,5-bis(1-aziridino-1-hydroxyiminomethyl)furan (16),
3,4-bis[(aziridinyl)-1-hydroxyiminomethyl]furoxane (17),
bis(2-methoxycarbonylaziridino)glyoxime (18),
bis(2-carbamoylaziridino)glyoxime (19),
2,2'-azinobis(1-aziridino-1-hydroxyiminomethyl)propane (20), and
2,2'-azinobis[1-(2-carbamoylaziridino)-1-hydroxyimino] propane (21).

Another subject of this invention is a method for preparing 1-aziridino-1-hydroxyiminomethyl derivatives pursuant to the invention, by reacting a halogen

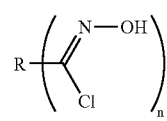

compound with the general formula II wherein R and n have the meanings given above, in a known way with an aziridine derivative with the general formula III

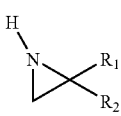

wherein $R_1$ and $R_2$ have the meanings given above.

The compounds of Formula I pursuant to the invention can be prepared by known methods according to the reaction diagram 1. To this end, nitriles with the general formula IV are converted to the carboxamide oximes with the general structure VI by reaction with hydroxylamine hydrochloride. By diazotization in hydrochloric acid medium, the chlorinated oximes of Structure II are obtained, which can then be converted to the compounds pursuant to the invention by reaction with aziridines of Formula III. Alternatively, as indicated in reaction diagram 1, the synthesis can be carried out starting with the carboxylic acids V by standard procedures described in the literature. The experimental method is indicated in the examples for the sequence IV→VI→II→I.

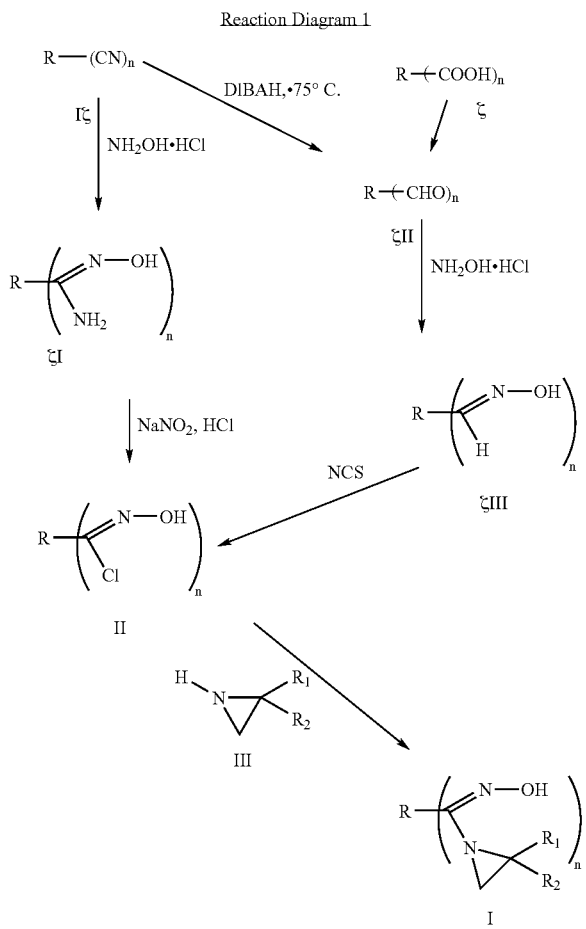

Another subject of this invention is drugs characterized by containing a compound according to the general formula I.

Also a subject of this invention are drugs for oral, rectal, subcutaneous, intravenous, or intramuscular administration that contain a compound with the general formula I in addition to conventional vehicles and diluents.

Suitable dosage forms and their preparation are known for themselves and are described, for example in "Hagers Handbuch der pharmazeutischen Praxis" (*Hager's Manual of Pharmaceutical Practice*), Springer Verlag—Berlin—Heidelberg, 1991, Volume 2, pp. 622 ff.

The drugs of the invention are prepared by known methods with the customary solid or liquid vehicles or diluents and the pharmaceutical adjuvants customarily used for the desired method of administration, in suitable doses. The preferred preparations consist of a dosage form that is suitable for oral administration. Examples of such dosage forms are tablets, film-coated tablets, sugar-coated tablets, capsules, pills, powders, solutions or suspensions, or depot forms.

Of course parenteral preparations such as solutions for injection are also practical. Suppositories should also be mentioned as examples of preparations.

Appropriate tablets can be obtained, for example, by mixing the active ingredient with known adjuvants, for example, inert diluents such as dextrose, sugar, sorbitol, mannitol, polyvinylpyrrolidone, disintegrants such as corn starch or alginic acid, binders such as starch or gelatin, lubricants such as magnesium stearate or talc, and/or agents for producing a depot effect such as carboxypolymethylene, carboxymethylcellulose, cellulose acetate phthalate, or polyvinyl acetate. The tablets can also consist of several layers. Correspondingly, sugar-coated tablets can be prepared by coating cores prepared similarly to the tablets with agents ordinarily used in coatings for sugarcoated tablets, for example polyvinylpyrrolidone or shellac, gum arabic, talc, titanium dioxide, or sugar. The shell of the sugar-coated tablet can also consist of several layers, for which the adjuvants mentioned above for tablets can be used.

Solutions or suspensions with the active ingredient pursuant to the invention can also contain, in addition, flavor-improving agents such as saccharin, cyclamate, or sugar, as well as flavorings such as vanillin or orange extract. The can also contain dispersants such as sodium carboxymethylcellulose or preservatives such as p-hydroxybenzoates. Capsules containing active ingredients can be prepared, for example, by encapsulating the active ingredient mixed with an inert carrier such as lactose or sorbitol in gelatin capsules.

Suitable suppositories can be prepared, for example, by mixing with vehicles intended for the purpose such as neutral fats or polyethylene glycol or their derivatives.

Of course transdermal therapeutic systems (TTSs) are also practical.

The compounds pursuant to the invention with the general formula I show antitumoral activity. The antitumoral activities of some compounds pursuant to the invention in the monolayer cytotoxicity test on selected cell lines are shown in Table 1. The low susceptibility of fibroblasts and endothelial cells with the use of the compounds pursuant to the invention is surprising.

Another subject of this invention is therefore the use of the 1-aziridino-1-hydroxyiminomethyl derivatives with the general formula I for preparing drugs for the treatment of tumors or cancerous diseases.

However, the use of the 1-aziridino-1-hydroxyiminomethyl derivatives according to the general formula I for the treatment of tumors or of cancerous diseases is also a subject.

Another subject of this invention is the use of 1,1'-[1,2-bis(hydroxyimino)-1,2-ethanediyl]bisaziridine (1) to prepare drugs for the treatment of tumors or of cancerous diseases, and that of 1,1'-[1,2-bis(hydroxyimino)-1,2-ethanediyl]bisaziridine (1) for the treatment of tumors or of cancerous diseases.

TABLE 1

Antitumoral activity of selected compounds pursuant to the invention

| Organ/cell line | Substance IC$_{50}$ [µg/ml] | 1 | 6 | 14 | 7 | 9 | 10 | 16 |
|---|---|---|---|---|---|---|---|---|
| Colon | HT29 | 0.486 | 0.117 | 0.200 | 0.258 | 0.329 | 0.670 | 0.481 |
| Stomach | GXF 251L | 0.781 | 0.020 | 0.717 | 0.542 | 1.506 | 3.964 | 1.661 |
| Lung | LXFL 529 | 0.441 | 0.027 | 0.006 | 0.038 | 0.063 | 0.100 | 0.099 |
| Breast | 401 NL | 0.040 | 0.207 | 0.011 | 0.018 | 0.060 | 0.043 | 0.039 |
| Kidney | 944 LL | 0.923 | 0.115 | 0.198 | 0.348 | 0.788 | 0.750 | 1.359 |
| Uterus | 1138 L | 0.173 | 0.014 | 0.034 | 0.038 | 0.066 | 0.111 | 0.073 |

The mean IC$_{50}$ values were determined for the compound 6 pursuant to the invention on a total of 12 cell lines (Table 3) compared to the therapy standard 5-fluorouracil (5FU) (See Table 2).

A clear superiority of the compound pursuant to the invention over the therapy standard is seen from these figures.

TABLE 2

Comparison of the antitumoral effect of (6) with the therapy standard 5-fluorouracil (5FU)

| Compound | IC$_{50}$ [µg/ml] |
|---|---|
| (6) | 0.030 |
| 5FU | 0.054 |

TABLE 3

Tumor cell lines used

| Tumor | Cell line |
|---|---|
| Breast | MAXF 401NL |
|  | MCF-7 |
| Colon | HT29 |
| Stomach | GXF251L |
| Lung | LXFA 629L |
|  | LXFE66L |
|  | LXFL529 |
| Melanoma | MEXF 462NL |
|  | MEXF 514L |
| Ovary | OVCAR3 |
| Kidney | RXF 944L |
| Uterus | UXF 1138L |

The following examples explain the invention.

EXAMPLES

Example 1

Preparation of 2,6-bis(1-aziridino-1-hydroxyiminomethyl)pyridine (6)

Pyridine-2,6-di(carboxamide oxime)

To a solution of hydroxylamine hydrochloride (18.07 g; 26 mmol) and NaOH (10.40 g; 26 mmol) in H$_2$O (90 ml) is added dropwise with vigorous stirring a solution of pyridine-2,6-dicarbonitrile (12.9 g; 10 mmol) in ethanol (60 ml). An exothermic reaction occurs, and stirring is then continued for 1.5 h at 40–50° C. After cooling, the precipitate is filtered off and washed with H$_2$O. Obtained after drying is 16.5 g (85% of the theoretical) of product. M.p. 237–239° C. $^1$H NMR. (DMSO-d$_6$: δ 6.20 (4H, s, NH$_2$); 7.76 (3H, s, C$_5$H$_3$N); 9.76 (2H, s, OH), —CHN (%) found: C, 43.6; H, 4.5; N, 35.9—calc.: C, 43.1; H, 4.6; N, 35.9.

Pyridine-2,6-dihydroxamic[acid]dichloride

To a cooled solution of pyridine-2,6-di(carboxamide oxime) (1.95 g; 10 mmol) in dilute HCl (20 ml conc. HCl+8 ml H$_2$O) is cautiously added dropwise with stirring a solution of NaNO$_2$ (1.78 g; 25 mmol) in H$_2$O (5 ml). After 1.5 h at 0–10° C., the solution is stirred for 12 h longer at room temperature. The precipitate is then filtered off and washed with H$_2$O. Obtained after drying is 2.0 g (79% of the theoretical) of product. M.p. 168–170° C. (dec.), —$^1$H NMR (DMSO-D$_6$): δ 8.00 (3H, s, C$_5$H$_3$N); 12.7 (2H, s, OH). —CHN (%) found C, 33.7; H, 2.2; N, 16.6—calc.: C, 33.3; H, 2.2; N, 16.7.

2,6-Bis(1-aziridino-1-hydroxyiminomethyl)pyridine (6)

To a solution of aziridine (0.65 g; 15 mmol) and N(C$_2$H$_5$)$_3$ (2.0 g; 20 mmol) in acetonitrile (20 ml) cooled to 0° C. is added dropwise with stirring a suspension of pyridine-2,6-dihydroxamic acid dichloride (1.26 g; 5 mmol) in CH$_3$CN (20 ml). The mixture is stirred for 90 min and the precipitated triethylamine hydrochloride is filtered off. The filtrate is evaporated under vacuum, and ethyl acetate is added. The mixture is filtered again and the product is washed with CHCl$_3$. Obtained is 0.76 g (60% of the theoretical) of product. M.p. 194–196° C. (dec.). $^1$H NMR: δ 2.31 (8H, s, CH$_2$); 7.73 (3H, S, C$_5$H$_3$N); 10.64 (2H, s, OH). CHN (%) found: C, 52.4; H, 5.3; N, 27.5 (C$_{11}$H$_{13}$N$_5$O$_2$×0.25H$_2$O)—calc.: C, 52.5; H, 5.4; N, 27.8.

The following compounds are obtained by an analogous method:

Example 2

1,4-Bis(1-aziridino-1-hydroxyiminomethyl)benzene (7)

M.p. 220–222° C. (dec.). $^1$H NMR: δ 2.20 (8H, s, CH$_2$); 7.00 (4H, s, C$_6$H$_4$); 12.6 (2H, s, OH). CHN (%) found: C, 58.3; H, 5.9: N, 22.4 (C$_{12}$H$_{14}$N$_4$O$_2$)— calc.: C, 58.5; H, 5.7; N, 22.7.

Example 3

1,4-Di(α-2-carbamoylaziridino-α-hydroxyiminomethyl)benzene (8)

M.p. 248–250° C. (dec.). $^1$H NMR: δ 2.36 (4H, s, CH$_2$); 2.82 (2H, m. CH); 7.16 and 7.47 (each 2H, s, s, NH$_2$); 7.64 (4H, s, C$_6$H$_4$); 10.6 (2H, s, OH). CHN (%) found: C, 50.3; H, 4.9; N, 24.9 (C$_{14}$H$_{16}$N$_6$O$_4$)— calc. C, 50.6; H, 4.8; N, 25.3.

Example 4

1,3-Bis(1-aziridino-1-hydroxyiminomethyl)benzene (9)

M.p. 179–181° C. (dec.). $^1$H NMR: δ 2.17 (8H, s, CH$_2$); 7.31 (1H, t, C$_6$H); 7.62 (2H, d, C$_6$H$_2$); 8.11 (1H, S, C$_6$H); 11.3 (2H, s, OH). CHN (%) found: C, 58.7; H, 5.8; N, 22.3 (C$_{12}$H$_{14}$N$_4$O$_2$)— calc.: C, 58.5; H, 5.7; N, 22.7.

Example 5

1,3,5-Tris(1-aziridino-1-hydroxyiminomethyl)benzene (10)

M.p.>300° C. (dec.). $^1$H NMR: δ 2.16 (12H, s, CH$_2$); 8.00 (3H, s, C$_6$H$_3$); 11.4 (3H, s, OH). CHN (%) found: C, 54.1; H, 5.4; N, 25.0 (C$_{15}$H$_{18}$N$_6$O$_3$)—calc.: C, 54.5; H, 5.5; N, 25.4.

Example 6

1,3-Di(α-2-carbamoylaziridino-α-hydroxyiminomethyl)benzene (11)

M.p. 209–211° C. (dec.). $^1$H NMR: δ 2.38 (4H, m, CH$_2$); 3.02 (2H, m, CH); 7.16 and 7.42 (each 2H, s, s, NH$_2$); 7.42 (1H, t, C$_6$H); 7.91 (1H, t, C$_6$H); 10.6 (2H, m, OH). CHN (%) found: C, 45.9; H, 5.3; N, 22.8 (C$_{14}$H$_{16}$N$_6$O$_4$×2H$_2$O)—calc.: C, 45.6; H, 5.5; N, 22.8.

Example 7

2,6-Di(α-2-carbamoylaziridino-α-hydroxyiminomethyl)pyridine (12)

M.p. 206–208° C. (dec.). $^1$H NMR: δ 2.38 (4H, m, CH$_2$); 2.96 (2H, m, CH); 7.11 and 7.40 (each 2H, ss, NH$_2$); 7.76 (3H, s, C$_5$H$_3$N); 10.78 (2H, s, OH). CHN (%) found: C, 46.6; H, 4.6; N, 29.0 (C$_{13}$H$_{15}$N$_7$O$_4$)—calc.: C, 46.8; H, 4.5; N, 29.4.

Example 8

3,5-Bis(1-aziridino-1-hydroxyiminomethyl)pyridine) (13)

M.p.>300° C. (dec.). $^1$H NMR: δ 2.27 (8H, s, CH$_2$); 8.29 (1H, t, 4-C$_5$HN); 8.78 (2H, d, 2,6-C$_5$H$_2$N); 11.7 (2H, s, OH). CHN (%) found: C, 53.7; H, 5.1; N, 28.2 (C$_{11}$H$_{13}$N$_5$O$_2$)—calc.: C, 53.4; H, 5.3; N, 28.3.

Example 9

2,5-Bis(1-aziridino-1-hydroxyiminomethyl)pyridine (14)

M.p. 190–192° C. (dec.). $^1$H NMR: δ 2.22 (4H, s, CH$_2$); 2.26 (4H, s, CH$_2$); 7.76 (1H, d, C$_5$HN); 7.96 (1H, d, C$_5$HN); 8.78 (1H, s, C$_5$HN); 11.7 (2H, s, OH). CHN (%) found: C, 53.8; H, 5.2; N, 28.0 (C$_{11}$H$_{13}$N$_5$O$_2$)—calc.: C, 53.4; H, 5.3; N, 28.3.

Example 10

2,4-Bis(1-aziridino-1-hydroxyiminomethyl)pyridine (15)

M.p.>300° C. (dec.). $^1$H NMR: δ 2.20 (8H, s, CH$_2$); 7.53 (1H, dd, C$_5$HN); 8.16 (1H, d, C$_5$HN); 8.51 (1H, d, C$_5$HN); 11.6 (1H, s, OH); 11.8 (1H, s, OH). CHN (%) found: C, 53.4; H, 5.5; N, 28.0 (C$_{11}$H$_{13}$N$_5$O$_2$)—calc.: C, 53.4; H, 5.3; N, 28.3.

Example 11

2,5-Bis(1-aziridino-1-hydroxyiminomethyl)furan (16)

M.p. 182–184° C. (dec.). $^1$H NMR: δ 2.22 (8H, s, CH$_2$); 6.78 (2H, s, C$_4$H$_2$O); 10.5 (2H, s, OH). CHN (%) found: C, 47.3; H, 5.6; N, 22.1 (C$_{10}$H$_{12}$N$_4$O$_4$)—calc.: C, 47.2; H, 5.6; N, 22.0.

Example 12

3,4-Bis[(aziridinyl-1)hydroxyiminomethyl]furoxane (17)

M.p.>300° C. (dec.). $^1$H NMR: δ 2.18 (4H, s, CH$_2$); 2.43 (4H, s, CH$_2$); 11.1 (1H, s, OH); 11.4 (1H, s, OH). CHN (%) found: C, 38.2; H, 4.2; N, 32.9 (C$_8$H$_{10}$N$_6$O$_4$)—calc.: C, 37.8; H, 4.0; N, 33.1.

Example 13

Bis(2-methoxycarbonylaziridino)glyoxime (18)

M.p. 212–214° C. $^1$H NMR: δ 2.36 (4H, m, CH$_2$); 2.96 (2H, m, CH); 3.62 (6H, s, CH$_3$); 10.71 (2H, s, OH). CHN (%) found: C, 42.3; H, 5.0; N, 19.3 (C$_{10}$H$_{14}$N$_4$O$_6$) calc.: C, 42.0; H, 4.9; N, 19.6.

Example 14

Bis(2-carbamoylaziridino)glyoxime (19)

M.p.>300° C. $^1$H NMR: δ 2.28 (1H, m, CH); 2.40 (1H, m, CH); 2.83 (1H, m, CH); 7.09 and 7.24 (each 1H, s, s, NH$_2$); 10.65 (1H, s, OH). CHN (%) found: C, 37.1; H, 4.8; N, 32.1 (C$_8$H$_{12}$N$_6$O$_4$)—calc.: C, 37.5; H, 4.7; N, 32.8.

Example 15

2,2'-Azinobis(1-aziridino-1-hydroxyimino)propane (20)

M.p. 172–174° C. $^1$H NMR: δ 1.91 (6H, s, CH$_3$); 2.20 (8H, s, CH$_2$); 10.9 (2H, s, OH). CHN (%) found: C, 46.4; H, 4.5; N, 32.2 (C$_{10}$H$_{16}$N$_6$O$_2$×0.5H$_2$O)—calc.: C, 46.0; H, 6.6; N, 32.2.

Example 16

2,2'-Azinobis[1-(2-carbamoylaziridino)-1-hydroxyimino]propane (21)

M.p. 242–244° C. (dec.). $^1$H NMR: δ 1.98 (6H, s, CH$_3$); 2.53 (2H, s, CH$_2$); 2.53 (2H, m, CH$_2$); 2.89 (2H, m, CH); 7.04 and 7.22 (each 2H, ss, NH$_2$); 11.02 (2H, S, OH). CHN (%) found: C, 41.6; H, 5.4; N, 32.1 ($C_{12}H_{18}N_8O_4 \times 0.5H_2O$)—calc.: C, 41.5; H, 5.5; N, 32.3.

Example 19 sic

To test the antiproliferative properties of the compounds pursuant to the invention, a modified propidium iodide assay (Dengler, W. A., Schulte, J., Berger, P. B., Mertelsmann, R., Fiebig, H. H.: Anti-Cancer Drugs 6, 522–532, (1995)) was carried out as described below:

Tumor cells from cell cultures in the exponential growth phase (RPMI Medium, 10% FCS) were harvested, counted, and transferred into 96-well microtiter plates (140 μL cell suspension, $1 \times 10^5$ or $5 \times 10^4$ cells/mL). After a period of 24 h in which the cells resumed their exponential growth, 10 μL of the test substance dissolved in medium was added to each well (each test concentration was determined in triplicate). After 3–6 days of incubation (depending on the rate of cell doubling), the culture medium was replaced by 200 μL of a fresh medium that contained propidium iodide (25 μg/mL). The microliter plates were then kept for 24 hours at –18° C. to achieve total cell death. After thawing the plates, fluorescence was measured by means of a Millipore Cytofluor 235 (excitation 530 nm, emission 620 nm). The $IC_{50}$ values of the test compounds were calculated according to the published formula. If an $IC_{50}$ could not be determined within the tested dosage units, the lowest or highest concentration tested was used in each case for the calculation.

The invention claimed is:

1. 1-Aziridino-1-hydroxyiminomethyl derivatives of formula I

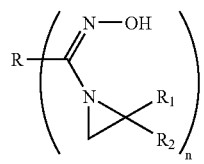

wherein

R is an organic group capable of bonding covalently two aziridine oxime groups and is selected from the group consisting of linear or branched, saturated or unsaturated alkanes or heteroalkanes with up to 6 carbon atoms and with up to four hetero atoms, and $C_3$–$C_8$ cycloalkanes, that are optionally substituted with lower $C_1$–$C_6$ alkyl, lower $C_1$–$C_6$ alkoxy, nitro, amino, monosubstituted amino or halogen groups, heterocyclic compounds with 3 to 6 ring atoms and up to four hetero atoms, aromatic compounds with up to 8 ring atoms, optionally substituted with cyano, hydroxy, lower $C_1$–$C_6$ alkyl, lower $C_1$–$C_6$ alkoxy, nitro, amino, monosubstituted amino, trihaloalkyl and/or halogen groups, and heteroaryls with 3 to 7 ring atoms and up to four hetero atoms, $R_1$ and $R_2$ independently of one another are selected from the group consisting of —H, —$CH_3$, —CN, —COOH, —$COOCH_3$, —$COOC_2H_5$, —$CONH_2$, or —$C_6H_5$ group, provided that each of $R_1$ and $R_2$ is not —H or —$CH_3$, when n is 2.

2. The compound of claim 1, wherein R is selected from the group consisting of methane, ethane, propane, butane, isobutane, pentane, isopentane, neopentane, hexane, azine, cyclopropane, cyclobutane, cyclopentane, cyclohexane, cycloheptane, cyclooctane, pyrrole, pyrroline, imidazole, imidazoline, pyrazolidine, thiazole, thiazoline, thiazolidine, isothiazole, isothiazoline, isothiazolidine, benzothiazole, furan, dihydrofuran, tetrahydrofuran, benzofuran, thiophene, benzothiophene, oxazole, oxazoline, oxazolidine, piperidine, piperazine, pyrimidine, morpholine, dihydropyran, tetrahydropyran, pyridazine, benzene, furoxane, imidazole, imidazoline, imidazolidine, pyrazole, pyrazoline, pyrazolidine, pyridine and pyridine N-oxide, dihydropyridine, pyrimidine, or pyrazine.

3. 1-Aziridino-1-hydroxyiminomethyl derivatives of formula I

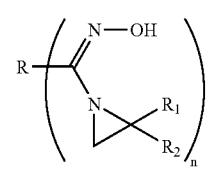

wherein

R is an organic group capable of bonding covalently two aziridine oxime groups, $R_1$ and $R_2$ independently of one another are selected from the group consisting of —H, —$CH_3$, —CN, —COOH, —$COOCH_3$ —$COOC_2H_5$, —$CONH_2$, or —$CH_6H_5$ group, provided that each of $R_1$ and $R_2$ is not —H or —$CH_3$, when n is 2, said 1-aziridino-1-hydroxyiminomethyl derivatives being selected from the group consisting of 2,6-bis(1-aziridino-1-hydroxyiminomethyl)pyridine, 1,4-bis(1-aziridino-1-hydroxyiminomethyl)benzene, 1,4-di(α-2-carbamoylaziridino-α-hydroxyiminomethyl)benzene, 1,3-bis(1-aziridino-1-hydroxyiminomethyl)benzene, 1,3-di(α-2-carbamoylaziridino-α-hydroxyiminomethyl)benzene, 2,6-di(α-2-carbamoylaziridino-α-hydroxyiminomethyl)pyridine, 3,5-bis(1-aziridino-1-hydroxyiminomethyl)pyridine, 2,5-bis(1-aziridino-1-hydroxyiminomethyl)pyridine, 2,4-bis(1-aziridino-1-hydroxyiminomethyl)pyridine, 2,5-bis(1-aziridino-1-hydroxyiminomethyl)furan, 3,4-bis[(aziridinyl)-1-hydroxyiminomethyl]furoxane, bis(2-methoxycarbonylaziridino)glyoxime, bis(2-carbamoylaziridino)glyoxime, 2,2'-azinobis(1-aziridino-1-hydroxyiminomethyl)propane, and 2,2'-azinobis[1-(2-carbamoylaziridino)-1-hydroxyimino]propane.

4. A method of treating tumors of or cancerous diseases of at least one of colon, stomach, lung, breast and uterus in humans which comprises administering to a human patient in need of treatment a therapeutically effective amount of a 1-aziridino-1-hydroxyiminomethyl derivative of formula I

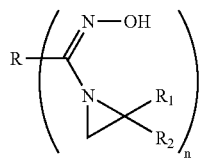

wherein

R is an organic group capable of bonding covalently two aziridine oxime groups, $R_1$ and $R_2$ independently of one another are selected from the group consisting of —H, —$CH_3$, —CN, —COOH, —$COOCH_3$, —$COOCH_2H_5$, —$CONH_2$, or —$C_6H_5$ group, provided that each of $R_1$ and $R_2$ is not —H or —$CH_3$, when n is 2.

5. A method of treating tumors of or cancerous diseases of at least one of colon, stomach, lung, breast and uterus in humans which comprises administering to a human patient in need of treatment a therapeutically effective amount of 1,1'-[1,2-bis(hydroxyimino)-1,2-ethanediyl]bisaziridine.

6. The compound of claim 1 wherein said $C_3$–$C_8$ cycloalkanes are substituted with at least one substituent selected from the group consisting of lower $C_1$–$C_6$ alkyl, lower $C_1$–$C_6$ alkoxy, nitro, amino, monosubstituted amino, and halogen groups.

* * * * *